(12) United States Patent
Sasayama

(10) Patent No.: US 7,256,328 B2
(45) Date of Patent: Aug. 14, 2007

(54) INBRED BROCCOLI LINE GKO-1

(75) Inventor: Junichi Sasayama, Kazo (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/217,019

(22) Filed: Aug. 31, 2005

(65) Prior Publication Data

US 2007/0050861 A1    Mar. 1, 2007

(51) Int. Cl.
- *A01H 5/00* (2006.01)
- *A01H 5/10* (2006.01)
- *A01H 4/00* (2006.01)
- *A01H 1/00* (2006.01)
- *C12N 15/82* (2006.01)

(52) U.S. Cl. .................. 800/306; 800/260; 800/266; 800/278; 800/279; 800/281; 800/300; 800/301; 800/302; 800/303; 435/410

(58) Field of Classification Search ............. 800/260, 800/269, 278, 279, 281, 306, 266, 300, 301, 800/302, 303; 435/410, 421, 430, 430.1
See application file for complete search history.

(56) References Cited

U.S. PATENT DOCUMENTS

| | | | | |
|---|---|---|---|---|
| 5,304,719 | A | * | 4/1994 | Segebart ............... 800/303 |
| 5,367,109 | A | * | 11/1994 | Segebart ............... 800/320.1 |
| 5,523,520 | A | | 6/1996 | Hunsperger et al. |
| 5,763,755 | A | * | 6/1998 | Carlone ............... 800/320.1 |
| 5,850,009 | A | * | 12/1998 | Kevern ............... 800/271 |
| 6,693,229 | B2 | * | 2/2004 | Sasayama et al. ....... 800/306 |

OTHER PUBLICATIONS

Poehlman, J.M. and D.A. Sleper. 1995. Breeding Field Crops. 4th ed. Iowa State University Press, Ames, Iowa, p. 473.*

Bennetzen, et al., 1992. Approaches and progress in the molecular cloning of plant disease resistance genes. *In* Genetic Engineering 14:99-124, Ed. J.K. Setlow, Plenum Press, NY.

Cheung, et al., 1997. Conservation of S-locus for self incompatibility in *Brassica napus* (*L.*) and *Brassica oleracea* (*L.*). Theor. Appl. Genet. 95:73-82.

Earle, et al., 1994. Cold-tolerant Ogura CMS Brassica vegetables for horticultural use. Cruciferase Newsletter 16:80-81.

Eshed, et al., 1996. Less-than-additive epistatic interactions of quantitative trait loci in tomato. Genetics 143:1807-1817.

Knott, et al., 1990. The role of biotechnology in canola/rapeseed research. *In* Rapeseed Production, Nutrition, and Technology, pp. 47-78, Van Reinold, NY.

Kraft, et al., 2000. Linkage disequilibrium and fingerprinting in sugar beet. Theor. App. Genet. 101:323-326.

Pang, et al., 1992. Expression of a gene encoding a scorpion insectotoxin peptide in yeast, bacteria and plants. Gene 116:165-172.

* cited by examiner

*Primary Examiner*—David H. Kruse
*Assistant Examiner*—Keith O. Robinson
(74) *Attorney, Agent, or Firm*—Jondle & Associates P.C.

(57) ABSTRACT

An inbred broccoli line, designated GKO-1 is disclosed. The invention relates to the seeds of inbred broccoli line GKO-1, to the plants of inbred broccoli line GKO-1, and to methods for producing a broccoli plant produced by crossing the inbred line GKO-1 with itself or another broccoli line. The invention further relates to hybrid broccoli seeds and plants produced by crossing the inbred line GKO-1 with another broccoli line. The invention further relates to methods for producing a broccoli plant containing in its genetic material one or more transgenes and to the transgenic plants produced by that method and to methods for producing other inbred broccoli lines derived from the inbred GKO-1.

33 Claims, No Drawings

INBRED BROCCOLI LINE GKO-1

BACKGROUND OF THE INVENTION

This invention relates to a new and distinctive broccoli inbred line, designated GKO-1. All publications cited in this application are herein incorporated by reference.

There are numerous steps involved in the development of any new and novel desirable germplasm with superior combining ability. Plant breeding begins with the analysis and definition of problems and weaknesses of the current germplasm, the establishment of program goals, and definition of specific breeding objectives. The next step is selection of germplasm that posseses the traits to meet the program goals and the best breeding method to reach those goals. The objective is to combine in a single inbred or hybrid an improved combination of desirable traits from the parental germplasm. These important characteristics may include higher yield, better flavor, improved color and field holding ability, resistance to diseases and insects along with economic seed yields to facilitate the cost of hybrid seed production.

The method chosen for breeding or selection depends on the mode of plant reproduction, the heritability of the trait(s) being improved, and the inbred used commercially (e.g. $F_1$ hybrid, pureline). The complexity of inheritance influences choice of breeding method. A most difficult task is the identification of individuals that are genetically superior, because for most traits other confounding plant traits or environmental factors mask the true genotypic value. One method of identifying a superior plant is to observe its performance relative to other experimental plants and to a widely grown standard cultivar. If a single observation is inconclusive, observations in multiple locations and seasons provide a better estimate of its genetic worth.

The development of commercial broccoli hybrids requires the development of homozygous inbred lines. Breeding programs combine desirable traits from two or more germplasm sources from which various broad based breeding gene pools are used to develop inbred lines; those inbred lines are created by selfing followed by selection of desired phenotypes sometimes utilizing anther, microspore and ovule culture to speed up and improve selection efficiency.

The goal of plant breeding is to develop new, unique, and superior broccoli cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line having the same broccoli traits.

Description of breeding methods that are commonly used for different traits and crops can be found in one of several reference books. (e.g. Allard, 1960; Simmonds, 1979; Sneep et. al., 1979; Fehr, 1987).

Proper testing and evaluation should detect any major faults and establish the level of superiority or improvement over current cultivars. In addition to showing superior performance, there must be a demand for a new cultivar that is compatible with industry standards or which creates a new market. For seed-propagated cultivars, it must be feasible to maintain the inbred lines and produce seed easily and economically.

Broccoli is a relatively new crop in North, South and Central America, Northern Europe and Asia. The introduction of hybrid cultivars in the 1960's provided a magnitude increase in yield, holding ability, plant uniformity, expanded growing seasons and large-scale production of broccoli. The goal in broccoli breeding is to make continued improvement in hybrid broccoli yields and horticultural characteristics in order to sustain the supply to meet continuous increase in demand for broccoli in developed and emerging world economies. To accomplish this goal new breeding methods such as anther culture and microspore culture have been utilized to more rapidly generate inbred broccoli lines from more diverse germplasm sources.

Broccoli (*Brassica oleracea*, Italica group) belongs to the mustard family. All *Brassica oleracea* will cross-pollinate. Pollination occurs via insect vectors, the most common of which is the honeybee. Broccoli, like most other *Brassicas*, has a genetic characteristic of self-incompatibility, which encourages cross pollination resulting in higher levels of variability. Variability in populations is desired for wide adaptation and survival. Broccoli breeding populations can be inbred or backcrossed and/or with the use of double haploids derived from anther culture to develop homozygous inbred lines. Broccoli $F_1$ hybrids can be produced by using self-incompatibility or cytoplasmic male sterility to control pollen movement between selected inbred lines.

Self-incompatibility is a breeding system that enforces outcrossing and therefore maximizes recombination in cross-pollinated species. This breeding system in nature has been utilized by humans in $F_1$ hybrid breeding, especially in *Brassica* vegetables (Tsunoda et al., chapter 13).

Cytoplasmic male sterility (CMS) is another method used in *Brassica* vegetable species to produce $F_1$ hybrids. This method of producing hybrids in *Brassica* is a more recent development compared to self-incompatibility. A genetic mutation contained in the cytoplasm (mitochondria) is responsible for the lack of production of pollen. In *Brassica*, the cytoplasm has commonly been identified in and transferred from "Ogura" radish (Ogura, 1968). The major advantage of CMS over self-incompatibility is that under normal conditions, no pollen is produced in the female parent. Theoretically, this results in the production of 100% hybrid seed. Under certain stressful growth conditions, however, it may be possible to produce small amounts of fertile pollen in CMS plants. *Brassica* inbreds containing CMS (sterile "A" lines) are maintained by continued hybridization to their normal (fertile) counterpart inbred, commonly referred to as a "B" line.

The plants associated with the *Brassica* group have been familiar to mankind since ancient times, and always of great agricultural importance. *Brassica* is a major food species worldwide. *Brassica* species have a general adaptation for cool climate growing conditions. Therefore, adaptation has occurred for summer growing conditions with cool to moderate climates and for winter growing conditions in warmer or tropical locations.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

The invention comprises a novel inbred broccoli line, designated GKO-1. This invention thus relates to the seeds of inbred broccoli line GKO-1, to the plants of inbred broccoli line GKO-1, to methods used for controlling pollination when making hybrid seed with GKO-1, to methods for producing a broccoli plant by crossing the inbred broccoli line GKO-1 with itself or another broccoli line, and to methods for producing a broccoli plant containing in its genetic material one or more transgenes and to the transgenic broccoli plants produced by that method. This invention further relates to hybrid broccoli seeds and plants produced by crossing the inbred line GKO-1 with another broccoli line.

The broccoli plant of this invention may further comprise, or have, a cytoplasmic factor or other factor that is capable of conferring male sterility. Male sterility may also be provided by nuclear genes such as the recessive ms gene. Parts of the broccoli plant of the present invention are also provided, such as e.g., pollen obtained from an inbred plant and an ovule of the inbred plant.

In another aspect, the present invention provides regenerable cells for use in tissue culture of inbred broccoli plant GKO-1. The tissue culture will preferably be capable of regenerating plants having essentially all of the physiological and morphological characteristics of the foregoing inbred broccoli plant, and of regenerating plants having substantially the same genotype as the foregoing inbred broccoli plant. Preferably, the regenerable cells in such tissue culture will be embryos, protoplasts, calli, meristematic cells, pollen, leaves, anthers, stems, petioles, roots, root tips, fruits, seeds, flowers, cotyledons, hypocotyls, or the like. Still further, the present invention provides broccoli plants regenerated from the tissue cultures of this invention.

Another objective of the invention is to provide methods for producing other inbred broccoli plants derived from inbred broccoli line GKO-1. Inbred broccoli lines derived by the use of those methods are also part of the invention.

The invention also relates to methods for producing a broccoli plant containing in its genetic material one or more transgenes and to the transgenic broccoli plant produced by that method.

In another aspect, the present invention provides for single gene converted plants of GKO-1. The single transferred gene may preferably be a dominant or recessive allele. Preferably, the single transferred gene will confer such trait as male sterility, herbicide resistance, insect resistance, resistance for bacterial, fungal, or viral disease, male fertility, improved harvest characteristic, enhanced nutritional quality, and improved processing characteristics. The single gene may be a naturally occurring broccoli gene or a transgene introduced through genetic engineering techniques.

The invention further provides methods for developing broccoli plants in a broccoli plant breeding program using plant breeding techniques including recurrent selection, backcrossing, pedigree breeding, restriction fragment length polymorphism enhanced selection, and genetic marker enhanced selection and transformation. Seeds, broccoli plants, and parties thereof produced by such breeding methods are also part of the invention.

In addition to the exemplary aspects and embodiments described above, further aspects and embodiments will become apparent by the study of the following descriptions.

DEFINITIONS

In the description and tables, which follow, a number of terms are used. In order to provide a clear and consistent understanding of the specification and claims, including the scope to be given such terms, the following definitions are provided.

Plant Height: Plant height is measured in centimeters from the soil line to the top of the leaves.

Head Height: Head height is measured in centimeters from the soil line to the top of the head.

Leaf Width: Leaf width is measured in centimeters at the midpoint of the plant including the petiole.

Leaf Length: Leaf length is measured in centimeters from the base of the leaf to the tip of the leaf from a leaf sampled from the midpoint of the plant and does not include the petiole in the measurement.

Head Diameter: Head Diameter is measured at the widest diameter of the head (from overhead) in centimeters.

Head Depth: Head Depth is measured in centimeters from the top of the head to the lowermost florets.

Stem Diameter: Stem diameter is measured in centimeters and is taken at a point just below the head.

Maturity: Plants are considered mature when the head and stem have developed to the fresh market maturity stage.

Yield: The yield is the weight in grams for a harvested broccoli head or floret cluster.

Overall Rating Score: This Overall Rating Score is rated on a scale of 1 to 5. A score of 5 indicated an excellent overall rating. A score of 3.0 indicates average, and a score of 1 indicates poor.

Color: Color means the color of the head at maturity.

Field Holding Ability: Field Holding Ability means the ability of a plant to maintain good head quality (i.e. small, firm, green heads) after the optimal harvest date.

Disease and Insect Ratings: Disease and Insects are rated on a scale of 1 to 5. A score of 5 indicates severe damage. A score of 3.0 indicates moderate damage, and a score of 1 indicates no damage.

Essentially all of the physiological and morphological characteristics. A plant having essentially all of the physiological and morphological characteristics means a plant having essentially all of the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

L:W Ratio. L:W ratio is the ratio of the leaf length to the leaf width; it is used to give a quick impression of the leaf shape.

Lodging. Lodging is a situation where a plant cannot support itself and has a tendency to lean toward or fall over onto the ground.

Bead Size. Bead size is the size of an individual floret in the head.

Bead Shape. Bead shape is the shape of an individual floret in the head.

Dome shape. Dome shape is the overall shape of the top of the head.

DETAILED DESCRIPTION OF THE INVENTION

Inbred broccoli GKO-1 is a heading broccoli (*Brassica oleracea* Italica group) with superior characteristics, and provides an excellent parental line in crosses for producing first generation ($F_1$) hybrid broccoli. GKO-1 is a late maturity inbred having very high yield potential when compared to lines of similar maturity. GKO-1 has excellent agronomic characteristics including a tighter head (florets and stalks are closer together making it more desirable for the crown-cut market), and better holding ability (the broccoli can remain mature in the field instead of being harvested immediately) when compared to commercial cultivar Heritage.

Some of the selection criteria used for various generations include a tight head, small bead size, no side-shoots on head, and less anthocyanin.

The inbred has shown uniformity and stability for all traits, as described in the following variety description information. The line has been increased and maintained by pollination with fertile inbred line GKO-1 (non-CMS) with continued observation for uniformity. No variant traits have been observed or are expected in GKO-1.

The inbred broccoli line GKO-1 has the following morphologic and other characteristics. The data were collected in the summer of 2005 in Salinas, Calif. Plants were approximately 105 days old and were planted with 12-inch spacing between the plants.

TABLE 1

VARIETY DESCRIPTION INFORMATION

| Plant: | |
| --- | --- |
| Maturity: | Late; between 100–105 days from sowing |
| Habit: | Upright |
| Height: | 30–35 cm |
| Leaves: | |
| Length: | 20–30 cm |
| Width: | 10–15 cm |
| L:W ratio: | 2:1 |
| Margin: | Wavy |
| Veins: | Thick |
| Anthocyanin: | Absent |
| Inflorescence: | |
| Bud size: | Small, tightly bunched |
| Flower color: | Yellow |
| Head diameter: | 18–25 cm |
| Head depth: | 10–15 cm |
| Stem diameter: | 5.0 cm |
| Head color: | Blue-green |

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred or line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed broccoli plants, using transformation methods as described below to incorporate transgenes into the genetic material of the broccoli plant(s).

Expression Vectors for Broccoli Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation that are not of bacterial origin include, for example, mouse dihydrofolate reductase, plant 5-enolpyruvyl-shikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

In vivo methods for visualizing GUS activity that do not require destruction of plant tissue are available. Molecular Probes publication 2908, Imagene Green, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in broccoli. Optionally, the inducible promoter is operably linked to a nucleotide sequence encoding a signal sequence which is operably linked to a gene for expression in broccoli. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Mett et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in broccoli or the constitutive promoter is operably linked to a nucleotide sequence encoding a signal sequence which is operably linked to a gene for expression in broccoli.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985)) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter1/Ncol fragment 5' to the *Brassica napus* ALS3 structural gene (or a nucleotide sequence similarity to said Xba1/Ncol fragment), represents a particularly useful constitutive promoter. See PCT application WO 96/30530.

C. Tissue-specific or Tissue-preferred Promoters—A tissue-specific promoter is operably linked to a gene for expression in broccoli. Optionally, the tissue-specific promoter is operably linked to a nucleotide sequence encoding a signal sequence which is operably linked to a gene for expression in broccoli. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217: 240–245 (1989)); a pollen-specific promoter such as that from Zm13 (Guerrero et al., *Mol. Gen. Genetics* 244: 161–168 (1993)) or a microspore-preferred promoter such as that from apg (Twell et al., *Sex. Plant Reprod.* 6:217–224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3–17 (1987); Lerner et al., *Plant Physiol.* 91:124–129 (1989); Fontes et al., *Plant Cell* 3:483–496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499–509 (1984); Steifel, et al., *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is a broccoli plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A gene conferring resistance to a pest, such as nematodes. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus*α-amylase inhibitor) and U.S. Pat. No. 5,494,813 (Hepher and Atkinson, issued Feb. 27, 1996).

G. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyper-accumulation of a monoterpene, a sesquiterpene, a steroid, a hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect*

Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes That Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., Theor. Appl. Genet. 83:435 (1992).

C. An herbicide that inhibits photosynthesis, such as a triazine (psbA and gs+genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes That Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased phytate content-1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteol. 170:810 (1988) (nucleotide sequence of *Streptococcus mutants* fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus lichenifonnis* α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley α-amylase gene), and Fisher et al., *Plant Physiol.* 102:1045 (1993) (maize endosperm starch branching enzyme II).

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611–622,1992).

Methods for Broccoli Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985), Christou et al., *Proc. Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues has also been described. Donn et al., In Abstracts of VIIth International Congress on Plant Cell and Tissue Culture IAPTC, A2–38, p 53 (1990); D'Halluin et al., *Plant Cell* 4:1495–1505 (1992) and Spencer et al., *Plant Mol. Biol.* 24:51–61 (1994).

Following transformation of broccoli target tissues, expression of the above-described selectable marker genes allows for preferential selection of transformed cells, tissues and/or plants, using regeneration and selection methods now well known in the art.

The foregoing methods for transformation would typically be used for producing a transgenic inbred. The transgenic inbred could then be crossed, with another (non-transformed or transformed) inbred, in order to produce a new transgenic inbred. Alternatively, a genetic trait which has been engineered into a particular broccoli line using the foregoing transformation techniques could be moved into another line using traditional backcrossing techniques that are well known in the plant breeding arts. For example, a backcrossing approach could be used to move an engineered trait from a public, non-elite inbred into an elite inbred, or from a inbred containing a foreign gene in its genome into an inbred or inbreds which do not contain that gene. As used herein, "crossing" can refer to a simple X by Y cross, or the process of backcrossing, depending on the context.

Single-Gene Conversion

When the term "broccoli plant" is used in the context of the present invention, this also includes any single gene conversions of that inbred. The term "single gene converted plant" as used herein refers to those broccoli plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term "backcrossing" as used herein refers to the repeated crossing of a hybrid progeny back to the recurrent parent, i.e., backcrossing 1, 2, 3, 4, 5, 6, 7, 8, 9 or more times to the recurrent parent. The parental broccoli plant which contributes the gene for the desired characteristic is termed the "nonrecurrent" or "donor parent". This terminology refers to the fact that the nonrecurrent parent is used one time in the backcross protocol and therefore does not recur. The parental broccoli plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a broccoli plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are genes for male sterility, some of which are inherited cytoplasmically, but still act as single gene traits. Several of these single gene traits are described in U.S. Pat. Nos. 5,777,196, 5,948,957, and 5,969,212, the disclosures of which are specifically hereby incorporated by reference.

Further reproduction of the inbred can occur by tissue culture and regeneration. Tissue culture of various tissues and regeneration of plants therefrom is well known and widely published. For example, reference may be had to Komatsuda, T. et al., *Crop Sci.* 31:333–337 (1991); Stephens, P. A., et al., *Theor. Appl. Genet.* 82:633–635 (1991); Komatsuda, T. et al., *Plant Cell, Tissue and Organ Culture*, 28:103–113 (1992); Dhir, S. et al. *Plant Cell Reports* 11:285–289 (1992); Pandey, P. et al., *Japan J. Breed.* 42:1–5 (1992); and Shetty, K., et al., *Plant Science* 81:245–251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce broccoli plants having essentially all of the physiological and morphological characteristics of inbred broccoli line GKO-1.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, described certain techniques.

This invention also is directed to methods for producing a broccoli plant by crossing a first parent broccoli plant with a second parent broccoli plant wherein the first or second parent broccoli plant is a broccoli plant of broccoli line GKO-1. Further, both first and second parent broccoli plants can come from the inbred broccoli line GKO-1. Thus, any such methods using inbred broccoli line GKO-1 are part of this invention: selfing, backcrosses, hybrid production, crosses to populations, and the like. All plants produced using inbred broccoli line GKO-1 as a parent are within the scope of this invention, including those developed from inbreds derived from inbred broccoli line GKO-1. Advantageously, the broccoli line could be used in crosses with other, different, broccoli plants to produce first generation ($F_1$) broccoli hybrid seeds and plants with superior characteristics. The inbred of the invention can also be used for transformation where exogenous genes are introduced and expressed by the inbred of the invention. Genetic variants created either through traditional breeding methods using inbred broccoli line GKO-1 or through transformation of inbred broccoli line GKO-1 by any of a number of protocols known to those of skill in the art are intended to be within the scope of this invention.

It should be understood that the inbred can, through routine manipulation of cytoplasmic or other factors, be produced in a male-sterile form. Such embodiments are also contemplated within the scope of the present claims.

The following describes breeding methods that may be used with inbred broccoli line GKO-1 in the development of further broccoli plants. One such embodiment is a method for developing GKO-1 progeny broccoli plants in a broccoli plant breeding program comprising: obtaining the broccoli plant, or a part thereof, of inbred broccoli line GKO-1, utilizing said plant or plant part as a source of breeding material and selecting a GKO-1 progeny plant with molecular markers in common with inbred broccoli line GKO-1 and/or with morphological and/or physiological characteristics selected from the characteristics listed in Tables 1, 2, and 3. Breeding steps that may be used in the broccoli plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of GKO-1 progeny broccoli plants, comprising crossing inbred broccoli line GKO-1 with another broccoli plant, thereby producing a population of broccoli plants, which, on average, derive 50% of their alleles from inbred broccoli line GKO-1. A plant of this population may be selected and repeatedly selfed or sibbed with a broccoli line resulting from these successive filial generations. One embodiment of this invention is the broccoli line produced by this method and that has obtained at least 50% of its alleles from inbred broccoli line GKO-1.

One of ordinary skill in the art of plant breeding would know how to evaluate the traits of two plant inbreds to determine if there is no significant difference between the two traits expressed by those varieties. For example, see Fehr and Walt, Principles of Cultivar Development, p 261–286 (1987). Thus the invention includes broccoli line GKO-1, progeny broccoli plants comprising a combination of at least two GKO-1 traits selected from the group consisting of those listed in Tables 1, 2, and 3 or the inbred broccoli line GKO-1 combination of traits listed in the Summary of the Invention or in the Detailed Description of the Invention, so that said progeny broccoli plant is not significantly different for said traits than inbred broccoli line GKO-1 as determined at the 5% significance level of when grown in the same environment. Using techniques described herein, molecular markers may be used to identify said progeny plant as a GKO-1 progeny plant. Mean trait values may be used to determine whether trait differences are significant, and preferably the traits are measured on plants grown under the same environmental conditions. Once such an inbred is developed, its value is substantial since it is important to advance the germplasm base as a whole in order to maintain or improve traits such as yield, disease resistance, pest resistance, and plant performance in extreme environmental conditions.

Progeny of inbred line GKO-1 may also be characterized through their filial relationship with inbred broccoli line GKO-1, as for example, being within a certain number of breeding crosses of inbred broccoli line GKO-1. A breeding cross is a cross made to introduce new genetics into the progeny, and is distinguished from a cross, such as a self or a sib cross, made to select among existing genetic alleles. The lower the number of breeding crosses in the pedigree, the closer the relationship between inbred broccoli line GKO-1 and its progeny. For example, progeny produced by the methods described herein may be within 1, 2, 3, 4 or 5 breeding crosses of inbred broccoli line GKO-1.

As used herein, the term "plant" includes plant cells, plant protoplasts, plant cells of tissue culture from which broccoli plants can be regenerated, plant calli, plant clumps, and plant cells that are intact in plants or parts of plants, such as pollen, flowers, seeds, stalks, stumps, leaves and the like. Thus, another aspect of this invention is to provide for cells, which upon growth and differentiation produce the inbred broccoli GKO-1.

When the term "broccoli plant" is used in the context of the present invention, this also includes any single gene conversions of that inbred. The term single gene converted plant as used herein refers to those broccoli plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental broccoli plants for that inbred. The parental broccoli plant which contributes the gene for the desired characteristic is termed the nonrecurrent or donor parent. This terminology refers to the fact that the nonrecurrent parent is used one time in the backcross protocol and therefore does not recur. The parental broccoli plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a broccoli plant is obtained wherein essentially all of the desired morphological and physiological characteristics of the recurrent parent are recovered in the converted plant, in addition to the single transferred gene from the nonrecurrent parent.

TABLES

In Table 2 shown below, the traits and characteristics of inbred broccoli line GKO-1 is given in hybrid combination and compared to commercial cultivar Heritage. The data collected on hybrids containing inbred broccoli line GKO-1 as a parent is presented. GKO-1 was tested in several hybrid combinations at different locations over a number of years. Column 1 shows the plant characteristic, column 2 shows the characteristics for the hybrid FBC0515, column three shows the characteristics for the hybrid FBC4420, column four shows the characteristics for the hybrid FBC2519, and column five shows the characteristics for commercial cultivar Heritage. The data were taken on plants approximately 105 days from transplanting into the field, spaced eight inches apart in Salinas, Calif. in July 2005 for the hybrids and in August 2005 for Heritage.

TABLE 2

| Characteristic | Hybrid | | | Commercial Cultivar |
| --- | --- | --- | --- | --- |
|  | FBC0515 | FBC4420 | FBC2519 | Heritage |
| Overall rating* | 5 | 3–4 | 5 | Not available |
| Dome shape | Domed, circular | Domed, circular | Domed, circular | Domed, circular |
| Habit | Upright | Upright | Upright | Upright |
| Lodging | Very little observed | Very little observed | Very little observed | Very little observed |
| Maturity | Late | Mid-late | Late in summer planting; very late in overwinter planting | Late |
| Color | Blue-green | Blue-green | Blue-green | Blue-green |
| Bead size | Small, tightly bunched | Small, tightly bunched | Small, tightly bunched | Small, tightly bunched |
| Bead shape | Round | Round | Round | Round |

*Measured on a scale of 1–5, where 1 = poor and 5 = best

In Table 3 shown below, the traits and characteristics of inbred broccoli line GKO-1 is given in hybrid combination and compared to commercial cultivar Heritage. The data collected on hybrids containing inbred broccoli line GKO-1 as a parent is presented. GKO-1 was tested in several hybrid combinations at different locations over a number of years. Column 1 shows the plant characteristic, column 2 shows the characteristics for the hybrid FBC0515, column three shows the characteristics for the hybrid FBC4420, column four shows the characteristics for the hybrid FBC2519, and column five shows the characteristics for commercial cultivar Heritage. The data were taken on plants approximately 95 days from transplanting into the field, spaced eight inches apart in Salinas, Calif. in August 2005.

TABLE 3

| Characteristic | Hybrid | | | Commercial Cultivar |
| --- | --- | --- | --- | --- |
| | FBC0515 | FBC4420 | FBC2519 | Heritage |
| Height (cm)* | 57–61 | 48–52 | 54–62 | 48–53 |
| Spread (cm) | 53–60 | 48–58 | 50–56 | 51–68 |
| Length (cm) | 28–33 | 27–38 | 36–37 | 31–34 |
| Width (cm) | 10–19 | 12–21 | 15–23 | 13–19 |
| L:W Ratio | About 2.3:1 | About 2:1 | About 2:1 | About 2:1 |
| Margin | Wavy | Wavy | Wavy | Wavy |
| Veins | Thick | Thick | Thick | Thick |
| Anthocyanin | Absent | Absent | Absent | Absent |
| Stem diameter (cm)** | 3–4 | 3–4 | 3–4 | 4–6 |
| Head color | Blue-green | Blue-green | Blue-green | Blue-green |

*Plant height is measured from the soil line to the tallest leaf.
**Stem diameter is measured on the stem between the soil line and the first leaf axil.

DEPOSIT INFORMATION

Deposits of the Sakata Seed Corporation proprietary inbred broccoli line GKO-1, hybrid broccoli seed FBC0515, hybrid broccoli seed FBC2519 and hybrid broccoli seed FBC4420 disclosed above and recited in the appended claims have been made with National Collections of Industrial Food and Marine Bacteria (NCIMB), 23 St. Machar Drive, Aberdeen, Scotland, AB24 3RY, United Kingdom. The date of deposit was Sep. 15, 2006 for proprietary inbred broccoli line GKO-1, hybrid broccoli seed FBC0515, hybrid broccoli seed FBC2519 and hybrid broccoli seed FBC4420. The deposits of 2,500 seeds each were taken from the same deposits maintained by Sakata Seed Corporation since prior to the filing date of this application. All restrictions upon the deposits have been removed, and the deposits are intended to meet all of the requirements of 37 § C.F.R. 1.801–1.809. The NCIMB accession number for inbred broccoli line GKO-1 is NCIMB 41436. The NCIMB accession number for hybrid broccoli seed FBC0515 is NCIMB 41437. The NCIMB accession number for hybrid broccoli seed FBC2519 is NCIMB 41438. The NCIMB accession number for hybrid broccoli seed FBC4420 is NCIMB 41439. The deposits will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed of inbred broccoli line designated GKO-1, wherein a representative sample of seed of said broccoli line was deposited under NCIMB No. 41436.

2. A broccoli plant, or a part thereof, produced by growing the seed of claim 1.

3. Pollen of the plant of claim 2.

4. An ovule of the plant of claim 2.

5. A tissue culture of cells produced from the plant of claim 2, wherein the cells of the tissue culture are from a plant part selected from the group consisting of embryos, protoplasts, meristematic cells, pollen, leaves, anthers, stems, petioles, roots, root tips, flowers, seeds, or beads.

6. A protoplast or callus produced from the tissue culture of claim 5.

7. A broccoli plant regenerated from the tissue culture of claim 5, wherein the plant has all of the morphological and physiological characteristics of inbred broccoli line GKO-1, wherein a representative sample of seed was deposited under NCIMB No. 41436.

8. A method for producing an $F_1$ hybrid broccoli seed, wherein the method comprises crossing the plant of claim 2 with a different broccoli plant and harvesting the resultant $F_1$ hybrid broccoli seed.

9. A method of producing an herbicide resistant broccoli plant wherein the method comprises transforming the broccoli plant of claim 2 with a transgene that confers resistance to an herbicide selected from the group consisting of imidazolinone, sulfonylurea, glyphosate, glufosinate, L-phosphinothricin, triazine and benzonitrile.

10. An herbicide resistant broccoli plant produced by the method of claim 9.

11. A method of producing an insect resistant broccoli plant wherein the method comprises transforming the broccoli plant of claim 2 with a transgene that confers insect resistance.

12. An insect resistant broccoli plant produced by the method of claim 11.

13. The broccoli plant of claim 12, wherein the transgene encodes a *Bacillus thuringiensis* endotoxin.

14. A method of producing a disease resistant broccoli plant wherein the method comprises transforming the broccoli plant of claim 2 with a transgene that confers disease resistance.

15. A disease resistant broccoli plant produced by the method of claim 14.

16. A method of producing a broccoli plant with modified fatty acid metabolism or modified carbohydrate metabolism wherein the method comprises transforming the broccoli plant of claim 2 with a transgene encoding a protein selected from the group consisting of phytase, fructosyltransferase, levansucrase, α-amylase, invertase and starch branching enzyme or encoding an antisense of stearyl-ACP desaturase.

17. A broccoli plant having modified fatty acid metabolism or modified carbohydrate metabolism produced by the method of claim 16.

18. A method of introducing a desired trait into inbred broccoli line GKO-1 wherein the method comprises:
 (a) crossing a GKO-1 plant, wherein a representative sample of seed was deposited under NCIMB No. 41436, with a plant of another broccoli line that comprises a desired trait to produce progeny plants wherein the desired trait is selected from the group consisting of male sterility, herbicide resistance, insect resistance, modified fatty acid metabolism, modified carbohydrate metabolism and resistance to bacterial disease, fungal disease or viral disease;
 (b) selecting one or more progeny plants that have the desired trait to produce selected progeny plants;
 (c) crossing the selected progeny plants with the GKO-1 plants to produce backcross progeny plants;
 (d) selecting for backcross progeny plants that have the desired trait and all of the physiological and morphological characteristics of broccoli line GKO-1 listed in Table 1 to produce selected backcross progeny plants; and
 (e) repeating steps (c) and (d) three or more times in succession to produce selected fourth or higher backcross progeny plants that comprise the desired trait and all of the physiological and morphological characteristics of broccoli line GKO-1 listed in Table 1.

19. A plant produced by the method of claim 18, wherein the plant has the desired trait and all of the physiological and morphological characteristics of broccoli line GKO-1 listed in Table 1.

20. The plant of claim 19, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

21. The plant of claim 19, wherein the desired trait is insect resistance and the insect resistance is conferred by a transgene encoding a *Bacillus thuringiensis* endotoxin.

22. The plant of claim 19, wherein the desired trait is modified fatty acid metabolism or modified carbohydrate metabolism and said desired trait is conferred by a nucleic acid encoding a protein selected from the group consisting of phytase, fructosyltransferase, levansucrase, α-amylase, invertase and starch branching enzyme or encoding an antisense of stearyl-ACP desaturase.

23. The plant of claim 19, wherein the desired trait is male sterility.

24. A hybrid broccoli seed designated FBC0515 having inbred broccoli line GKO-1 as a parental line, wherein a representative sample of seed of said hybrid was deposited under NCIMB No. 41437.

25. A hybrid broccoli plant produced by growing the hybrid broccoli seed of claim 24.

26. A hybrid broccoli seed designated FBC4420 having inbred broccoli line GKO-1 as a parental line, wherein a representative sample of seed of said hybrid was deposited under NCIMB No. 41439.

27. A hybrid broccoli plant produced by growing the hybrid broccoli seed of claim 26.

28. A hybrid broccoli seed designated FBC2519 having inbred broccoli line GKO-1 as a parental line, wherein a representative sample of seed of said hybrid was deposited under NCIMB No. 41438.

29. A hybrid broccoli plant produced by growing the hybrid broccoli seed of claim 28.

30. A method for producing a male sterile broccoli plant comprising transforming the broccoli plant of claim 2 with a nucleic acid molecule that confers male sterility.

31. A male sterile broccoli plant produced by the method of claim 30.

32. A hybrid broccoli seed produced by the method of claim 8.

33. A hybrid broccoli plant, or a part thereof, produced by growing said hybrid seed of claim 32.

* * * * *